United States Patent [19]

Minato et al.

[11] 3,946,020

[45] Mar. 23, 1976

[54] PROCESS FOR PRODUCING PYRIDINE BASES

[75] Inventors: Yoshizo Minato, Nishinomiya; Shikibu Nishikawa, Osaka, both of Japan

[73] Assignee: Koei Chemical Co., Ltd., Osaka, Japan

[22] Filed: Aug. 5, 1974

[21] Appl. No.: 495,001

Related U.S. Application Data

[63] Continuation of Ser. No. 211,710, Dec. 23, 1971, abandoned.

[30] Foreign Application Priority Data

Dec. 28, 1970  Japan.............................. 46-130303

[52] U.S. Cl............. 260/290 P; 252/449; 252/453; 252/454; 252/456; 252/457
[51] Int. Cl.²............ C07D 213/08; C07D 213/10; C07D 213/12
[58] Field of Search.................................... 260/290

[56] References Cited
UNITED STATES PATENTS

| | | | |
|---|---|---|---|
| 3,280,040 | 10/1966 | Jaffe................................ | 252/455 R |
| 3,317,438 | 5/1967 | Engebretson et al........... | 252/455 R |
| 3,375,064 | 3/1968 | Miale et al....................... | 252/455 R |
| 3,381,011 | 4/1968 | Hall.................................. | 260/290 |

FOREIGN PATENTS OR APPLICATIONS

| | | | |
|---|---|---|---|
| 2,064,397 | 7/1971 | Germany............................ | 260/290 |
| 2,054,773 | 5/1971 | Germany............................ | 260/290 |
| 900,799 | 7/1962 | United Kingdom................ | 260/290 |
| 1,069,368 | 5/1967 | United Kingdom................ | 260/290 |
| 1,188,891 | 4/1970 | United Kingdom................ | 260/290 |
| 1,563,467 | 4/1969 | France................................ | 260/290 |

*Primary Examiner*—Harry I. Moatz
*Attorney, Agent, or Firm*—Ladas, Parry, Von Gehr, Goldsmith & Deschamps

[57] ABSTRACT

Pyridine bases are produced in higher yield from at least one of aliphatic carbonyl compounds and ammonia by reaction at 350° to 550°C under the atmospheric pressure at a space velocity of 100 to 10,000 hr$^{-1}$ in the presence of a catalyst prepared by immersing silica-alumina or a silica-alumina mixture containing a promoter in an aqueous solution of ammonium halide such as ammonium chloride, ammonium iodide or ammonium bromide at a concentration of not more than 20% by weight at room temperature to 80°C, washing the immersed silica-alumina or the mixture with water, and drying and calcining the same at 300°C or higher. Regeneration of the catalyst after the reaction can be carried out for a much shortened time.

5 Claims, No Drawings

PROCESS FOR PRODUCING PYRIDINE BASES

This is a continuation of application Ser. No. 211,710 filed Dec. 23, 1971, now abandoned.

This invention relates to a process for producing pyridine bases, and more particularly to a process for producing pyridine bases from at least one of aliphatic carbonyl compounds and ammonia as main raw materials by using a novel catalyst.

Heretofore, silica-alumina has been usually used as a catalyst in the production of pyridine bases by a gas phase catalytic reacton of aldehydes and ammonia, but sometimes, several metallic oxides and fluorides have been used as a promoter (British patent specification No. 790,994, Japanese patent publication No. 89409/69). Further, there has been known a process for producing pyridine bases from an aliphatic ketone and ammonia by using calcium nickel phosphate as a catalyst (U.S. Pat. No. 3,412,096). However, the yields of the pyridine bases based on these catalysts are not satisfactory yet.

As a result of various studies on the catalysts, the present inventors have found that pyridine bases can be produced in higher yield from at least one of carbonyl compounds and ammonia as main raw materials by a gas phase catalytic reaction when a catalyst prepared by immersing silica-alumina or a silica-alumina mixture containing metallic oxides or fluorides as a promoter in a dilute aqueous solution of ammonium halide, washing the immersed silica-alumina or the silica-alumina mixture with water, and drying the same is used, than when a catalyst prepared without said immersion treatment is used. Furthermore, the present inventors have found that in reactivation of deactivated catalyst by supplying air to the catalyst and removing deposited carbon materials by burning after the reaction, that is, the so-called catalyst regeneration, the immersion treatment of the catalyst with the aqueous ammonium halide solution of the present invention is effective in reduction in the deposition of carbon materials onto the catalyst, and therefore, the regeneration times can be shortened and the efficiency of a reactor can be considerably improved in the present inventon.

An object of the present invention is to provide a process for preparing a novel catalyst for production of pyridine bases from at least one of aliphatic carbonyl compounds and ammonia as main raw materials, which comprises immersing silica-alumina or a silica-alumina mixture containing a metallic oxide such as thorium, lead, cadmium, or zinc, or a metallic fluoride such as manganese fluoride, bismuth fluoride or lead fluoride as a promoter, in an aqueous ammonium halide solution, washing the silica-slumina or the silica-alumina mixture with water, and drying and calcining the same.

Another object of the present invention is to provide a novel catalyst prepared according to the above-mentioned process.

Other object of the present invention is to provide a process for producing pyridine bases from at least one of aliphatic carbonyl compounds and ammonia as main raw materials by using a novel catalyst prepared according to the above-mentioned process The ammonium halide compounds used herein include ammonium iodide, ammonium chloride and ammonium bromide. Preferable concentration of the aqueous ammonium halide solution for the present immersion treatment is not more than 20% by weight, particularly 0.3 to 10% by weight.

Temperature for the immersion treatment is not particularly restricted, but the immersion time can be shortened when the immersion treatment is carried out at room temperature to 80°C. As the immersion time, 30 minutes to 5 days are sufficient. The immersed catalyst is thoroughly washed with water, and then dried and calcined at 300°C or higher. The thus prepared catalyst can be used in the reaction.

As the silica-alumina for the ammonium halide immersion treatment of the present invention, silica-alumina alone or a mixture of silica-alumina containing said metallic oxide or fluoride as a promoter can be used. Any process can be used to prepare the silica-alumina, for example, a process based on mixing of silica gel and alumina gel in a wet state, a process based on simultaneous gelation of silica and alumina from their aqueous solution and other various processes.

Further, there is no special restriction to a method for mixing the promoter. Preferable silica-alumina compozition has a ratio of silica to alumina of 95–70 : 5–30 by weight. When a metallic oxide is mixed with the silica-alumina as a promoter, it is preferable to add not more than 10% by weight of the oxide to the silica-alumina based on the weight of the silica-alumina. In the case metallic fluoride, it is preferable to add 0.1 to 30% by weight of the fluoride to the silica-alumina, based on the weight of the silica-alumina.

The aliphatic carbonyl compounds herein used include formaldehyde, acetaldehyde, propionaldehyde, acrolein, crotonaldehyde, acetone, diethylketone, methylethylketone, etc. In other words, any carbonyl compound can be used, so long as it can react with ammonia to form pyridine bases. Furthermore, para-aldehyde, para-formaldehyde, trioxane, methylal, diacetone alcohol, etc., which can be converted to an aldehyde or ketone by thermal decomposition or the like, can be also used.

It is preferable to use 0.2 to 5 moles of ammonia to one mole of total carbonyl compound.

Further, methanol or other third component can be used in addition to said main raw materials, the carbonyl compounds and ammonia. The reaction of the carbonyl compound with ammonia is carried out according to the ordinary gas phase catalytic reaction, and can be effected in a fixed bed, fluidized fed or moving bed. Preferable reaction temperature is 350° to 550°C. Preferable reaction pressure is the atmospheric pressure, but the pressure can be reduced or increased up to 2 kg/cm². Preferable space velocity (SV) of the raw material gas mixture is 100 to 10,000 hr⁻¹. The space velocity is defined by the following formula:

$$\frac{\text{Volume of feed gas mixture (ml)}}{\text{Volume of catalyst (ml)} \times \text{reaction time (hr)}}$$

The volume of feed gas mixture is based on the normal conditions, i.e. 0°C, 1 atmosphere.

Such pyridine bases as pyridine, picoline, lutidine, collidine, etc. can be produced in the present invention. For example, when formaldehyde and acetaldehyde are used together with ammonia, pyridine and 3-picoline are obtained. When formaldehyde and propionaldehyde are used together with ammonia, 3,5-lutidine and a small amount of 3-picoline are obtained. When formaldehyde, acetaldehyde and propionaldehyde are used together with ammonia, pyridine, 3-picoline and 3,5-lutidine are obtained. Further, when formaldehyde and acetone are used together with ammonia, 2,6-lutidine is principally obtained. When diethylketone or methylethylketone is used together with ammonia, 2,6-diethyl-3-methylpyridine or 2,3,6-trimethylpyridine is obtained.

Now, the effect of the present invention is shown below, referring to examples and reference examples.

| Raw materials | Treated with aqueous ammonium halide solution (The process of the present invention) | | | Not treated with aqueous ammonium halide solution | | |
|---|---|---|---|---|---|---|
| | Ex. | Total yield of pyridine bases (%) | Catalyst regeneration time (hour) | Ref. Ex. | Total yield of pyridine bases (%) | Catalyst regeneration time (hour) |
| Acetaldehyde, formaldehyde, ammonia | 1 | 67.3 | 3 | 1 | 52.4 | 5 |
| Acetaldehyde, formaldehyde, propionaldehyde, ammonia | 2 | 62.9 | 2 | 2 | 55.9 | 6 |
| Acetaldehyde, formaldehyde, ammonia | 4 | 62.6 | 2.5 | 3 | 59.4 | 3.5 |

Note-1:
$$\text{Yield} = \frac{\text{Amount of carbon in pyridine bases}}{\text{Amount of carbon in the raw material carbonyl compounds}} \times 100$$

Note-2: Catalyst regeneration time — time required by passing air over a catalyst untill the concentration of carbon dioxide gas in the effluent gas becomes 1% by volume or less, while adjusting the amount of air so that the temperature may not exceed 560°C over the catalyst.

As is clear from the foregoing table, the yield is 4.4 to 14.9% increased by carrying out the immersion treatment of the catalyst according to the present invention, and also that the catalyst regeneration time can be shortened by 1 to 4 hours. It is seen how distinguished the effect of the present invention is.

Now, the present invention will be explained in detail, referring to examples, but the present invention is not restricted to these examples.

EXAMPLE 1

An aqueous 6% aluminum nitrate solution containing 324 g of aluminum nitrate, $Al(NO_3)_3 \cdot 9H_2O$ and an aqueous 15% sodium silicate solution containing 356 g of silicon oxide were mixed together to form a slurry of aluminum hydroxide and silicic acid gel. The resulting slurry mixture was washed with water until there was no soluble salt contained therein, and dried at 110°C under aeration. 400 Grams of the thus obtained pellets having a ratio of silica to alumina of 89:11 by weight and having particle sizes of 3 mm was immersed in 800 g of an aqueous 5% ammonium iodide solution at room temperature, for example, 25° to 30°C, for 4 days, then thoroughly washed with water to remove iodine ions, and dried at 120°C. 500 ml of the thus prepared silica-alumina catalyst was filled in a tubular reactor, and a gas mixture consisting of 12 moles of formaldehyde, 12 moles of acetaldehyde and 26.4 moles of ammonia preheated to 200°C was passed through the tubular reactor for 3 hours (SV = 1,160 hr$^{-1}$), while keeping the tubular reactor at 420°C. The reaction gas mixture passed through the catalyst layer was cooled, and subjected to condensation. The resulting condensate was dehydrated with caustic soda, and 492 g of the thus obtained oil was distilled and quantitatively determined by gas chromatograph. The yields of the thus obtained reaction products were 38.1% pyridine (2.74 moles), 25.9% 3-picoline (1.55 moles) and 3.3% 3,5-lutidine (0.17 mole) on the basis of the amount of carbon of the aldehyde used. After the completion of the reaction, the catalyst was regenerated by burning the carbons deposited on the catalyst with air at 560°C or less. The required regeneration time was 3 hours.

EXAMPLE 2

400 Grams of silica-alumina powders having a ratio of silica to alumina of 87:13 by weight prepared in the same manner as in Example 1 was immersed in 800 g of an aqueous 1% ammonium chloride solution at room temperature for 2 hours, then thoroughly washed with water, dried at 120°C and shaped by tableting. 500 ml of the thus prepared catalyst was packed in a tubular reactor, and a gas mixture consisting of 13 moles of formaldehyde, 11 moles of acetaldehyde, 3 moles of propionaldehyde and 32 moles of ammonia preheated to 200°C was passed through the reactor at 440°C for 3 hours (SV = 1,330 hr$^{-1}$). The resulting yields based on the amount of carbon of the aldehydes used were 20.9% pyridine (1.84 moles), 32.9% 3-picoline (2.41 moles) and 9.1% 3,5-lutidine (0.57 mole). The time required for regenerating the catalyst with air at 560°C or less was about 2 hours.

EXAMPLE 3

320 g of pellets of silica-alumina having a ratio of silica to alumina of 85:15 by weight and having diameters of 3 mm, which were prepared in the same manner as in Example 1, were immersed in 640 g of an aqueous 5% ammonium bromide solution at room temperature for 5 days, washed with water and dried at 120°C. 500 ml of the thus prepared silica-alumina catalyst was packed in a tubular reactor, and a gas mixture consisting of a 3 moles of formaldehyde, 6 moles of propionaldehyde and 9 moles of ammonia was passed through the reactor at 440°C for 3 hours (SV = 372 hr$^{-1}$). The resulting yields based on the amount of carbon of the aldehydes used were 8.1% 3-picoline (0.28 mole) and 54.7% 3,5-lutidine (1.64 moles). The time required for regenerating the catalyst with air at 560°C or less was 3 hours.

EXAMPLE 4

The silica-alumina slurry prepared in the same manner as in Example 1 was washed with water, and mixed with an aqueous solution containing 0.4 mole of potassium fluoride, and further a dilute nitric acid solution containing 0.06 mole of bismuth nitrate was added thereto dropwise over a period of 20 minutes. The resulting slurry was washed with water, then dried at 110°C, shaped and calcined at 500°C for 5 hours. 400 Grams of the resulting three-component catalyst having a ratio of silica : alumina : bismuth fluoride of 89 : 11 : 8 was dipped in a solution mixture consisting of 450 g of an aqueous 0.3% ammonium iodide solution and 450 g of an aqueous 0.3% ammonium chloride solution at room temperature for 6 days. After the immersion, the catalyst was washed with water, dried at 120°C and calcined. 550 ml of the thus obtained catalyst was filled in a tubular reactor, and a gas mixture consisting of 8 moles of formaldehyde, 8 moles of acetaldehyde and 16 moles of ammonia was passed through the reactor at 450°C for 2 hours (SV = 1,030 hr$^{-1}$). The resulting yields based on the amount of carbons of the aldehydes used were 38.6 % pyridine (1.85 moles), 21.6% 3-picoline (0.87 mole) and 2.4% 3,5-lutidine (0.08 mole). The time required for regenerating the catalyst with air at 560°C or less was 2.5 hours.

EXAMPLE 5

A hydrogel slurry mixture of silica-alumina prepared in the same manner as in Example 1 was washed with water, dried at 100°C, shaped into pellets having diameters of 3 mm and calcined at 400°C for 4 hours. 400 Grams of the resulting catalyst having a ratio of SiO$_2$ to Al$_2$O$_3$ of 89:11 by weight was immersed in 800 cc of an aqueous 2.5% ammonium iodide solution at room temperature for 2 days, then thoroughly washed with water, dried at 120°C and calcined at 500°C for 3 hours. 550 ml of the thus prepared catalyst was filled in a tubular reactor, and a gas mixture consisting of 4 moles of formaldehyde, 8 moles of acetone and 12 moles of ammonia preheated to 200°C was passed through the reactor at 470°C over a period of 2 hours (SV = 670 hr$^{-1}$). The resulting yield based on the amount of carbon of the raw material carbonyl compound used was 37.3% 2,6-dimethylpyridine (1.49 moles).

70 Grams (1.20 moles) of unreacted acetone was separated and recovered from the reaction product solution by distillation. When the acetone recovery is taken into account, the yield will be 43.8%.

The time required for regenerating the catlayst with air at 560°C or less was 1.5 hours.

EXAMPLE 6

400 Grams of pellets of silica-alumina having a ratio of silica to alumina of 91:9 by weight and having diameters of 3 mm, which were prepared in the same manner as in Example 1, were immersed in 800 g of an aqueous 10% ammonium bromide solution at room temperature for 4 days, washed with water, dried at 120°C for 5 hours and calcined at 500°C for 5 hours. 550 cc of the thus prepared catalyst was filled in a tubular reactor, and a gas mixture consisting of 1.5 moles of formaldehyde, 3.0 moles of acetaldehyde, 8.1 moles of ammonia, 67.2 l of air and 24 moles of steam was passed through the reactor at 420°C over a period of 3 hours (SV = 537 hr$^{-1}$). The resulting yields based on the amount of carbon of the aldehydes used were 57.0% pyridine (0.85 mole) and 2.8% 3-picoline (0.035 mole). The time required for regenerating the catalyst with air at 560°C or less was 2.5 hours.

EXAMPLE 7

400 Grams of pellets of silica-alumina prepared in the same manner as in Example 1 was immersed in 800 g of an aqueous 5% ammonium bromide solution at room temperature for 2 days, then washed with water, dried at 120°C and further immersed in 800 g of an aqueous 5% ammonium iodide solution at room temperature for 2 days. 550 ml of the thus prepared catalyst was filled in a tubular reactor, and a gas mixture consisting of 3.4 moles of acrolein, 18 moles of ammonia, 400 l of air and 1,100 l of nitrogen was passed through the reactor at 420°C for 2 hours (SV = 1,800 hr$^{-1}$). The resulting yields based on the amount of carbon of the acrolein used were 52.2% pyridine (1.06 moles) and 8.3% 3-picoline (0.14 mole). The time required for regenerating the catalyst with air at 560°C or less was 3 hours.

EXAMPLE 8

616 Grams of a aqueous 6.5% sodium silicate solution and 675 g of an aqueous 10% aluminum nitrate solution were mixed together with stirring, and the resulting silica-alumina hydrogel was admixed with 250 g of an aqueous 30% zinc nitrate solution and 360 g of an aqueous 25% ammonia solution. The resulting mixture of having a ratio of silica : alumina : zinc oxide of 80.1 : 13.5 : 6.4 by weight was dried at 110°C and shaped to pellets having diameters of 3 mm. The thus prepared pellets were immersed in 1,000 cc of an aqueous 4% ammonium chloride solution at 60°C for 6 hours, then washed with water, dried at 120°C, then immersed further in 1,000 cc of an aqueous 1% ammonium iodide solution at 60°C for 6 hours, washed with water, dried at 120°C and calcined at 450°C for 3 hours.

550 ml of the thus prepared catalyst was filled in a tubular reactor, and a gas mixture having a molar ratio of acetaldehyde to ammonia of 1:1 was passed through the reactor at 450°C over a period of 3 hours (SV = 1,000 hr$^{-1}$). 540 g/hr of acetaldehyde was fed to the reactor. The resulting yields based on the amount of carbon of the acetaldehyde used were 35.7% 2-picoline (0.438 mole) and 27.4% 4-picoline (0.336 mole). The time required for regenerating the catalyst with air at 560°C or less was 1.5 hours.

Reference Example 1

An aqueous solution containing 324 g of aluminum nitrate and an aqueous water-glass solution containing 356 g of silicon oxide were mixed together to prepare a slurry of silica-alumina. The resulting slurry was washed with water, dried at 110°C, shaped and calcined at 500°C for 5 hours, whereby a catalyst having a ratio of SiO$_2$ to Al$_2$O$_3$ of 89:11 was obtained.

550 ml of the thus obtained catalyst was filled in a tubular reactor, and a gas mixture consisting of 12 moles of formaldehyde, 12 moles of acetaldehyde and 26.4 moles of ammonia preheated to 200°C was passed through the reactor at 450°C over a period of 3 hours (SV = 1,060 hr$^{-1}$). The resulting yields, based on the amount of carbon of the raw material aldehydes were 30.0% pyridine (2.16 moles), 20.6% 3-picoline (1.24 moles) and 1.8% 3,5-lutidine (0.09 mole). After the reaction, carbon materials deposited on the catalyst were burned with air at 560°C or less. The time required for regenerating the catalyst was 5 hours.

Reference Example 2

500 ml of the silica-alumina catalyst having a ratio of silica to alumina of 87:13 prepared in the same manner as in Reference Example 1 was filled in a tubular reactor, and a gas mixture consisting of 13 moles of formaldehyde, 11 moles of acetaldehyde, 3 moles of propionaldehyde and 32 moles of ammonia, preheated to 200°C was passed through the reactor at 440°C over a period of 3 hours (SV = 1,330 hr$^{-1}$). The resulting yields, based on the amount of carbon of the aldehydes used were 19.4% pyridine (1.71 moles), 28.5% 3-picoline (2.09 moles) and 8.0% 3,5-lutidine (0.50 mole). The time required for regenerating the catalyst after the reaction with air at 560°C or less was 6 hours.

Reference Example 3

The hydrogel slurry of silica-alumina obtained in the same manner as in Reference Example 1 was washed with water and admixed with an aqueous solution containing 0.4 mole of potassium fluoride, and further a dilute nitric acid solution containing 0.06 mole of bismuth nitrate was added thereto dropwise over a period of 20 minutes. The resulting slurry was washed with water, dried at 110°C, shaped to pellets having diameters of 3 mm and calcined at 500°C for 5 hours, whereby a catalyst having a ratio of $SiO_2 : Al_2O_3 : BiF_3$ of 89 : 11 : 8 was prepared.

550 ml of the thus prepared catalyst was filled in a tubular reactor, and a gas mixture consisting of 8 moles of formaldehyde, 8 moles of acetaldehyde and 16 moles of ammonia was passed through the reactor at 420°C over a period of 2 hours (SV = 1,030 hr$^{-1}$). The resulting yields, based on the amount of carbon of the aldehydes used, were 36.7% pyridine (1.76 moles), 20.6% 3-picoline (0.825 mole) and 2.1% 3,5-lutidine (0.072 mole). The time required for regenerating the catalyst with air at 560°C or less was 3.5 hours.

What is claimed is:

1. A process for producing pyridine bases, which comprises reacting at least one aliphatic carbonyl compound selected from the group consisting of formaldehyde, acetaldehyde, propionaldehyde, acrolein and acetone with 0.2 to 5 moles of ammonia per mole of the total carbonyl compounds in a gas phase at 350°C to 550°C at atmospheric pressure at a space velocity of 100 to 10,000 hr$^{-1}$ in the presence of a catalyst consisting essentially of 95 to 70% by weight of silica and 5 to 30% by weight of alumina obtained by immersing silica-alumina in an aqueous solution of ammonium chloride, ammonium bromide or ammonium iodine at 25 to 80°C for 30 minutes to 5 days, washing with water, drying and calcining at 300°C or higher.

2. A process according to claim 1, wherein the said aliphatic carbonyl compound is a mixture of formaldehyde and acetaldehyde.

3. A process according to claim 1, wherein the said aliphatic carbonyl compound is a mixture of formaldehyde, acetaldehyde and propionaldehyde.

4. A process according to claim 1, wherein the said aliphatic carbonyl compound is acrolein.

5. A process according to claim 1, wherein the said aliphatic carbonyl compound is a mixture of formaldehyde and acetone.

* * * * *